(12) United States Patent
Kinoshita et al.

(10) Patent No.: US 6,444,780 B1
(45) Date of Patent: Sep. 3, 2002

(54) METHOD OF PRODUCING POLYETHERESTER MONOMER AND CEMENT DISPERSANTS

(75) Inventors: Mitsuo Kinoshita; Kazuhisa Okada, both of Aichi (JP)

(73) Assignee: Takemoto Yushi Kabushiki Kaisha, Aichi (JP)

( * ) Notice: Subject to any disclaimer, the term of this patent is extended or adjusted under 35 U.S.C. 154(b) by 105 days.

(21) Appl. No.: 09/660,699

(22) Filed: Sep. 13, 2000

(30) Foreign Application Priority Data

Oct. 8, 1999 (JP) .......................................... 11-287542
Jul. 27, 2000 (JP) ...................................... 2000-226606

(51) Int. Cl.$^7$ ............................................. C08G 64/00
(52) U.S. Cl. ...................................... 528/271; 528/272
(58) Field of Search ................................. 528/176, 271, 528/272

(56) References Cited

U.S. PATENT DOCUMENTS 5,362,829 A * 11/1994 Kinoshita et al. ............... 524/5

* cited by examiner

Primary Examiner—Terressa M. Boykin
(74) Attorney, Agent, or Firm—Beyer Weaver & Thomas LLP

(57) ABSTRACT

Polyetherester monomer of the kind

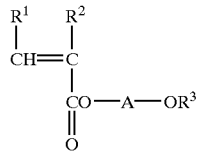

where $R^1$, $R^2$ and $R^3$ are each a group of a specified kind and A is a residual group of another specified kind is produced by an esterification reaction of polyalkyleneglycol with a closed end and unsaturated carboxylic acid, each of a specified kind, by using an acid catalyst under a heated and reduced-pressure condition in the absence of solvents and in the presence of a specified amount of p-benzoquinone and/or phenothiazine. Cement dispersants with improved properties are obtained from water-soluble vinyl monomers produced by using the polyetherester monomer thus obtained as intermediate product.

22 Claims, No Drawings

METHOD OF PRODUCING POLYETHERESTER MONOMER AND CEMENT DISPERSANTS

BACKGROUND OF THE INVENTION

This invention relates to a method of producing polyetherester monomer and cement dispersion agents (or cement dispersants). It has been known to produce polyetherester monomer as an intermediate product by an esterification reaction of polyalkyleneglycol with a closed end and unsaturated carboxylic acid and to copolymerize this polyetherester monomer with vinyl monomers which are copolymerizable therewith to obtain vinyl copolymers that can be used widely as a dispersant, an antistatic agent, an antifogging agent, an emulsifier or an adherent. In such applications, the quality of the monomer to be used in such a copolymerization reaction, and in particular the quality of polyetherester monomer, is known to significantly affect the quality of the produced vinyl copolymer serving as a dispersant, an antistatic agent, an antifogging agent, an emulsifier or an adherent. In other words, if the quality of polyetherester monomer obtained as the intermediate product is not sufficiently high, vinyl copolymers produced therefrom cannot function satisfactorily as a dispersant, an antistatic agent, an antifogging agent, an emulsifier or an adherent.

U.S. Pat. Nos. 4,962,173 and 5,362,829, for example, disclosed water-soluble vinyl copolymers having polyalkyleneglycol chain as a side chain serving as cement dispersants capable of providing a superior fluidity characteristic with a small slump loss to hydraulic cement compositions such as mortar and concrete. Such a water-soluble vinyl copolymer is usually produced by first preparing polyetherester monomer as an intermediate product by an esterification reaction of polyalkyleneglycol with a closed end and unsaturated carboxylic acid and then copolymerizing it with vinyl monomers capable of copolymerizing therewith. In this case, the quality as a cement dispersant of the water-soluble vinyl copolymer which is obtained is significantly dependent on the quality of the monomer, and in particular that of polyetherester monomer, that is used in the copolymerization reaction. In other words, if the polyetherester monomer serving as an intermediate product is of a poor quality, fluidity cannot be provided to a satisfactory manner to a hydraulic cement composition when the water-soluble vinyl copolymer obtained therefrom is used as a cement dispersant. The fluidity which has been provided has a large slump loss in such a case, and products obtained by hardening such a hydraulic cement composition have a low compressive strength.

As disclosed in Japanese Patent Publication Tokkai 11-71151, such polyetherester monomers as described above have conventionally been produced by using an organic solvent with a low boiling point such as benzene in an esterification reaction of polyalkyleneglycol with a closed end and unsaturated carboxylic acid. Use of such an organic solvent with a low boiling point is advantageous in that it is possible to obtain polyetheresters of a fairly high quality. On the other hand, the solvent which has been used for the reaction must be collected and the cost of equipment therefor adds to the total production cost of the polyetherester, or that of the vinyl copolymer to be used as the intermediate product and that of the water-soluble vinyl copolymers serving as a cement dispersant. In addition, the workers will be forced to work in an undesirable environment due to some of the properties of these substances.

SUMMARY OF THE INVENTION

It is therefore an object of this invention to provide a method of producing polyetherester monomer of a high quality without using a solvent.

It is another object of this invention to provide water-soluble vinyl copolymers capable of serving as a cement dispersant with improved properties, obtainable from such polyetherester monomer.

The present inventors discovered, as a result of work in view of the above objects, firstly that polyetherester monomer of a high quality can be obtained by an esterification reaction of polyalkyleneglycol with a closed end and unsaturated carboxylic acid under a specified condition in the presence of a specified amount of p-benzoquinone and/or phenothiazine and in the absence of any solvent, and secondly that water-soluble vinyl copolymers obtained by a radical copolymerization reaction of this polyetherester monomer with vinyl monomers which are copolymerizable therewith in an aqueous solution have improved properties as a cement dispersant.

DETAILED DESCRIPTION OF THE INVENTION

This invention relates, on one hand, to a method of producing polyetherester monomer shown by Formula 3 given below, by causing an esterification reaction of polyalkyleneglycol with a closed end shown by Formula 1 given below and unsaturated carboxylic acid shown by Formula 2 given below by using an acid catalyst under a heated and reduced-pressure condition in the absence of solvents and in the presence of p-benzoquinone and/or phenothiazine in an amount of 0.03–0.5 weight % of polyalkyleneglycol with a closed end while distilling away generated water, where Formulas 1, 2 and 3 are respectively:

(Formula 1)

(Formula 2)

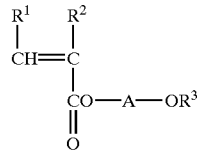
(Formula 3)

where $R^1$ and $R^2$ are each H or methyl group, $R^3$ is alkyl group with 1–22 carbon atoms, benzyl group, phenyl group or alkylphenyl group having alkyl group with 1–12 carbon atoms, and A is residual group obtained by removing all hydroxyl groups from polyalkyleneglycol of which the repetition number of oxyalkylene units (consisting either only of oxyethylene units or of both oxyethylene units and oxypropylene units) being 5–250. This invention relates, on the other hand, to cement dispersants characterized as comprising water-soluble vinyl copolymer obtained by a radical copolymerization reaction of polyetherester monomer produced by a method described above and vinyl monomers that can be copolymerized therewith.

According to this invention, explained more in detail, polyalkyleneglycol with a closed end shown by Formula 1 and unsaturated carboxylic acid shown by Formula 2 are caused to undergo an esterification reaction in the absence of a solvent to obtain polyetherester monomer shown by Formula 3. Examples of $R^3$ in Formula 1 for polyalkyleneglycol with a closed end include (1) alkyl groups with 1–22 carbon atoms such as methyl group, ethyl group, propyl group, isopropyl group, butyl group, hexyl group, octyl group, decyl group, dodecyl group, tetradecyl group, hexadecyl group, octadecyl group, eicosanyl group and docosanyl group; (2) benzyl group; (3) phenyl group; and (4) alkylphenyl groups having alkyl group with 1–12 carbon atoms such as methylphenyl group, ethylphenyl group, propylphenyl group, isopropylphenyl group, butylphenyl group, hexylphenyl group, octylphenyl group, nonylphenyl group and dodecylphenyl group. Among these, however, alkyl groups with 1–12 carbon atoms and benzyl group are preferable and alkyl groups with 1–3 carbon atoms are even more preferable.

As for A in Formulas 1 and 3, examples thereof include (1) residual groups obtained by removing all hydroxyl groups from polyethyleneglycol of which the oxyalkylene units are all oxyethylene units and (2) residual groups obtained by removing all hydroxyl groups from polyethylene-polypropyleneglycol of which the oxyalkylene units include both oxyethylene units and oxypropylene units, but residual groups obtained by removing all hydroxyl groups from polyethyleneglycol are preferred. If residual groups obtained by removing all hydroxyl groups from polyethylene-polypropyleneglycol are used as A, the repetition of its oxyethylene and oxypropylene units may be by random and/or block connections. The repetition number of the oxyalkylene units in the residual group representing A is 5–250, and is preferably 7–90.

Examples of polyalkyleneglycol with a closed end shown by Formula 1 include methoxy polyethyleneglycol, methoxy polyethyleneglycol-polypropyleneglycol, ethoxy polyethyleneglycol, ethoxy polyethyleneglycol-polypropyleneglycol, propoxy polyethyleneglycol, propoxy polyethyleneglycol-polypropyleneglycol, butoxy polyethyleneglycol, lauryloxy polyethyleneglycol, butoxy polyethyleneglycol-polypropyleneglycol, benzyloxy polyethyleneglycol, benzyloxy polyethyleneglycol-polypropyleneglycol, phenoxy polyethyleneglycol, phenoxy polyethyleneglycol-polypropyleneglycol, alkylphenoxy polyethyleneglycol, and alkylphenoxy polyethyleneglycol-polypropyleneglycol.

Examples of unsaturated carboxylic acid shown by Formula 2 include methacrylic acid, acrylic acid and crotonic acid. Among these, methacrylic acid is desirable.

According to this invention, polyetherester monomer shown by Formula 3 is obtained by causing polyalkyleneglycol with a closed end shown by Formula 1 and unsaturated carboxylic acid shown by Formula 2 as explained above to undergo an esterification reaction by using an acid catalyst under a heated and reduced-pressure condition in the absence of solvents and in the presence of p-benzoquinone and/or phenothiazine while distilling away generated water. The amount of p-benzoquinone and/or phenothiazine to be present in this reacting system should be 0.03–0.5 weight %, and preferably 0.1–0.25 weight %, of polyalkyleneglycol with a closed end shown by Formula 1. In particular, the presence of p-benzoquinone in an amount of 0.1–0.25 weight % of polyalkyleneglycol with a closed end shown by Formula 1 is preferable. If the amount of p-benzoquinone and/or phenothiazine present in the reacting system is less than 0.03 weight % of polyalkyleneglycol with a closed end shown by Formula 1, there is not sufficient effect of preventing polymerization. If it is greater than 0.5 weight %, on the other hand, the effect of preventing polymerization is sufficient but the radical copolymerization reaction does not proceed smoothly when the polyetherester monomer thus obtained is used as an intermediate product to produce vinyl copolymers.

The heating at the time of the aforementioned esterification reaction should preferably be to the temperature range of 105–135° C. and the pressure in the range of 15–0.5 kPa. The heating and the lowering of the pressure should preferably be carried out either continuously or in a stepwise manner within the ranges given above.

Examples of the acid catalyst to be used in the esterification reaction include sulfuric acid, p-toluene sulfonic acid, phosphoric acid and methane sulfonic acid. They may be used either singly or as a mixture but it is preferable to use sulfuric acid singly or a mixed acid of sulfuric acid and p-toluene sulfonic acid. The amount of the acid catalyst to be used is preferably 0.2–1.5 weight % of the total of polyalkyleneglycol with a closed end shown by Formula 1 and unsaturated carboxylic acid shown by Formula 2.

The ratio between the amounts of polyalkyleneglycol with a closed end shown by Formula 1 and unsaturated carboxylic acid shown by Formula 2 to be used in the esterification reaction should preferably be 1/1.5–1/7 (in molar ratio). After the esterification reaction, the excess portion of unsaturated carboxylic acid is distilled away.

The method of producing polyetherester monomer according to this invention is explained next further in detail. When methoxy polyethyleneglycol methacrylate, for example, is produced as the polyetherester monomer of this invention, methoxy polyethyleneglycol and an excess amount of methacrylic acid are placed inside a reactor and a specified amount of p-benzoquinone and/or phenothiazine serving as a polymerization inhibitor, appropriate for the amount of the methoxy polyethyleneglycol and a specified amount of concentrated sulfuric acid serving as an acid catalyst are added into the reactor. Next, the temperature of the reacting system is gradually raised and its pressure is gradually lowered until a specified temperature-pressure condition is reached. An esterification reaction is carried out under this temperature-pressure condition while water which is generated is removed by azeotropic distillation of water and methacrylic acid. After the esterification reaction, the excess portion of methacrylic acid is removed to obtain methoxy polyethyleneglycol methacrylate. The polyetherester monomer thus obtained contains the aforementioned polymerization inhibitor and acid catalyst but it may be directly used as an intermediate product for the production of vinyl copolymers without refining to remove them.

Next, cement dispersants according to this invention will be described. The cement dispersants of this invention are characterized as comprising water-soluble vinyl copolymers obtained through the following two steps, the first step being that of obtaining polyetherester monomer shown by Formula 3 as described above, that is, by causing an esterification reaction of polyalkyleneglycol with a closed end shown by Formula 1 and unsaturated carboxylic acid shown by Formula 2 by using an acid catalyst under a heated and reduced-pressure condition in the absence of solvents and in the presence of p-benzoquinone and/or phenothiazine in an amount of 0.03–0.5 weight % of the polyalkyleneglycol with a closed end while distilling away generated water, and the second step being that of obtaining water-soluble vinyl copolymers by a radical copolymerization reaction of the polyetherester monomer obtained in the first step with vinyl monomers which are copolymerizable with it inside an aqueous solution.

Any of known kinds of vinyl monomers can be used in the second step as long as they are copolymerizable with polyetherester monomer. Examples of such vinyl monomer include ethylenic unsaturated monocarboxylic acids and/or their salts, ethylenic unsaturated dicarboxylic acids and/or their salts, ethylenic unsaturated monocarboxylic acid esters, unsaturated carboxylic acid esters with hydroxyl group, aromatic vinyl monomers, vinyl monomers with amino group, vinyl monomers with amide group, vinyl monomers with aldehyde group, vinyl monomers with nitrile group, vinyl esters, alkene compounds, dien compounds and vinyl monomers having sulfonic acid group. Among these, ethylenic unsaturated monocarboxylic acids and/or their salts and vinyl monomers with sulfonic acid group are desirable. Particularly preferable are (1) (meth)acrylic acids and/or their salts such as (meth)acrylic acid, alkali metal salts of (meth)acrylic acid, alkali earth metal salts of (meth)acrylic acid and organic amine salts of (meth)acrylic acid, and (2) methallyl sulfonic acid salts to be used with such (meth)acrylic acids and/or their salts such as alkali metal salts of methallyl sulfonic acid, alkali earth metal salts of methallyl sulfonic acid and organic amine salts of methallyl sulfonic acid.

The invention does not impose any particular limitation on the copolymerization ratios of polyetherester monomer and vinyl monomers which are copolymerizable therewith but in the case of radical copolymerization of polyetherester monomer and (meth)acrylic acid and/or its salt, it is preferable to copolymerize 5–50 molar % of polyetherester monomer with 50–95 molar % of (meth)acrylic acid and/or its salt (such that the total will be 100 molar %), while in the case of radical copolymerization of polyetherester monomer, (meth)acrylic acid and/or its salt and methallyl sulfonic acid salt, it is preferable to copolymerize 5–45 molar % of polyetherester monomer, 50–90 molar % of (meth)acrylic acid and/or its salt and 0.3–15 molar % of methallyl sulfonic acid (such that the total will be 100 molar %).

The radical copolymerization reaction itself can be carried out in a known manner such as described, for example, in Japanese Patent Publication Tokkai 8-290948. Water-soluble vinyl copolymer can be obtained, for example, by preparing an aqueous solution containing polyetherester monomer obtained in the first step, vinyl monomers which are copolymerizable therewith and a chain transfer agent and causing a radical copolymerization reaction for 4–8 hours at reaction temperature of 50–90° C. in a nitrogen environment by adding a radical initiator. Examples of chain transfer agent which may be used in this process include 2-mercaptoethanol, mercaptopropionic acid and mercaptoacetic acid. Examples of radical initiator include persulfates such as sodium persulfate, potassium persulfate and ammoniumn persulfate and water-soluble radical initiators such as 2,2'-azobis(2-amidinopropane)dihydrochloride.

The average numerical molecular weight (hereinafter Pullulan converted by GPC method) of the water-soluble vinyl copolymers thus obtained by radical copolymerization is preferably 3500–70000 and more preferably 5000–40000.

Cement dispersants embodying this invention which comprises the water-soluble vinyl copolymers may be used for many kinds of hydraulic cement compositions using not only cement but also a mixing material in a fine powder form as a binder, or mortar and concrete as typical examples. Examples of cement include different kinds of portland cement such as normal portland cement, high early portland cement and moderate heat portland cement, as well as many different kinds of blended cement such as portland blast-furnace slag cement, fly ash cement and silica pozzolan cement. Examples of mixing material in a fine powder form include lime stone powder, calcium carbonate, silica fume, blast-furnace slag powder and fly ash.

The rate at which the cement dispersants of this invention should be used is normally 0.01–2.5 weight parts and preferably 0.05–1.5 weight parts % (by solid component) for 100 weight parts of binder consisting of cement or cement and mixing powder material.

The method of producing polyetherester monomer embodying this invention is characterized in that no solvent is used in the esterification reaction of polyalkyleneglycol with a closed end shown by Formula 1 and unsaturated carboxylic acid shown by Formula 2. As an important result of this, there is no need to collect any solvent after the esterification reaction is completed. Moreover, the method of this invention is capable of producing polyetherester monomer of a high quality shown by Formula 3. As will be described in detail below, polyetherester monomer with high esterification reaction rate can be obtained without abnormal increase in viscosity or generation of gel at the time of the esterification reaction. Water-soluble vinyl copolymers using high-quality polyetherester monomer produced by a method of this invention as an intermediate product exhibit desirable characteristics as cement dispersant. They can provide fluidity to hydraulic cement compositions with only a small slump loss and hardened products obtained from such hydraulic cement compositions have improved compressive strength.

The invention is described next by way of the following seven ((1)–(7)) examples of method embodying the invention.

(1) Method of obtaining polyetherester monomer (P-1) without using a solvent by causing esterification reaction with 1.0 mole of methoxy polyethyleneglycol (with repetition number of oxyethylene units equal to 9, hereinafter written as n=9) and 2.0 moles of methacrylic acid in the presence of p-benzoquinone in an amount corresponding to 0.21 weight % of this methoxy polyethyleneglycol (n=9) under the condition of temperature 125–130° C. and pressure 12–2.5 kPa and by using sulfuric acid as catalyst in an amount corresponding to 0.23 weight % of the total of methoxy polyethyleneglycol (n=9) and methacrylic acid while removing generated water by distillation and thereafter removing the excess amount of methacrylic acid by distillation.

(2) Method of obtaining polyetherester monomer (P-2) without using a solvent by causing esterification reaction with 1.0 mole of methoxy polyethyleneglycol (n=23) and 3.5 moles of methacrylic acid in the presence of p-benzoquinone in an amount corresponding to 0.18 weight % of this methoxy polyethyleneglycol (n=23) under the condition of temperature 125–130° C. and pressure 10–2.5 kPa and by using sulfuric acid as catalyst in an amount corresponding to 0.49 weight % of the total of methoxy polyethyleneglycol (n=23) and methacrylic acid while removing generated water by distillation and thereafter removing the excess amount of methacrylic acid by distillation.

(3) Method of obtaining polyetherester monomer (P-3) without using a solvent by causing esterification reaction with 1.0 mole of methoxy polyethyleneglycol (n=75) and 3.6 moles of methacrylic acid in the presence of p-benzoquinoine in an amount corresponding to 0.15 weight % of this methoxy polyethyleneglycol (n=75) under the condition of temperature 125–130° C. and pressure 7–1.5 kPa and by using sulfuric acid as catalyst in an amount corresponding to 0.31 weight % of the total of methoxy polyethyleneglycol (n=75) and methacrylic acid while removing generated water by distillation and thereafter removing the excess amount of methacrylic acid by distillation.

(4) Method of obtaining polyetherester monomer (P-4) without using a solvent by causing esterification reaction with 1.0 mole of benzyloxy polyethyleneglycol (n=90) and 3.2 moles of methacrylic acid in the presence of p-benzoquinone in an amount corresponding to 0.13 weight % of this benzyloxy polyethyleneglycol (n=90) under the condition of temperature 125–130° C. and pressure 5–1.5 kPa and by using a mixed liquid of sulfuric acid/p-toluene sulfonic acid=5/2 (in weight ratio) as catalyst in an amount corresponding to 0.68 weight % of the total of benzyloxy polyethyleneglycol (n=90) and methacrylic acid while removing generated water by distillation and thereafter removing the excess amount of methacrylic acid by distillation.

(5) Method of obtaining polyetherester monomer (P-5) without using a solvent by causing esterification reaction with 1.0 mole of lauryloxy polyethyleneglycol (n=120) and 5.0 moles of methacrylic acid in the presence of p-benzoquinone in an amount corresponding to 0.15 weight % of this lauryloxy polyethyleneglycol (n=120) under the condition of temperature 125–130° C. and pressure 5–1.5 kPa and by using a mixed liquid of sulfuric acid/p-toluene sulfonic acid=5.5/2.5 (in weight ratio) as catalyst in an amount corresponding to 0.80 weight % of the total of lauryloxy polyethyleneglycol (n=120) and methacrylic acid while removing generated water by distillation and thereafter removing the excess amount of methacrylic acid by distillation.

(6) Method of obtaining polyetherester monomer (P-6) without using a solvent by causing esterification reaction with 1.0 mole of methoxy polyethyleneglycol (n=23) and 3.5 moles of methacrylic acid in the presence of phenothiazine in an amount corresponding to 0.19 weight % of this methoxy polyethyleneglycol (n=23) under the condition of temperature 125–130° C. and pressure 10–2.5 kPa and by using a mixed liquid of sulfuric acid/p-toluene sulfonic acid=4.5/2.5 (in weight ratio) as catalyst in an amount corresponding to 0.47 weight % of the total of methoxy polyethyleneglycol (n=23) and methacrylic acid while removing generated water by distillation and thereafter removing the excess amount of methacrylic acid by distillation.

(7) Method of obtaining polyetherester monomer (P-7) without using a solvent by causing esterification reaction with 1.0 mole of methoxy polyethyleneglycol (n=75) and 4.1 moles of methacrylic acid in the presence of a mixture p-benzoquinone/phenothiazine=50/50 (in weight ratio) in an amount corresponding to 0.16 weight % of this methoxy polyethyleneglycol (n=75) under the condition of temperature 125–130° C. and pressure 5–1.5 kPa and by using a mixed liquid of sulfuric acid/p-toluene sulfonic acid=4/3 (in weight ratio) as catalyst in an amount corresponding to 0.54 weight % of the total of methoxy polyethyleneglycol (n=75) and methacrylic acid while removing generated water by distillation and thereafter removing the excess amount of methacrylic acid by distillation.

Next, the invention is described by way of the following 14 ((8)–(21)) examples of cement dispersant embodying the invention:

(8) Cement dispersant comprising water-soluble vinyl copolymer with average numerical molecular weight of 12500 obtained by radical copolymerization of aforementioned polyetherester monomer (P-1) and methacrylic acid at the ratio of 35/65 (in molar %) in an aqueous solution.

(9) Cement dispersant comprising water-soluble vinyl copolymer with average numerical molecular weight of 8800 obtained by radical copolymerization of aforementioned polyetherester monomer (P-1), sodium methacrylate and sodium methallyl sulfonate at the ratio of 33/61/6 (in molar %) in an aqueous solution.

(10) Cement dispersant comprising water-soluble vinyl copolymer with average numerical molecular weight of 17000 obtained by radical copolymerization of aforementioned polyetherester monomer (P-2) and methacrylic acid at the ratio of 35/65 (in molar %) in an aqueous solution.

(11) Cement dispersant comprising water-soluble vinyl copolymer with average numerical molecular weight of 9600 obtained by radical copolymerization of aforementioned polyetherester monomer (P-2), sodium methacrylate and sodium methallyl sulfonate at the ratio of 33/61/6 (in molar %) in an aqueous solution.

(12) Cement dispersant comprising water-soluble vinyl copolymer with average numerical molecular weight of 25300 obtained by radical copolymerization of aforementioned polyetherester monomer (P-3) and methacrylic acid at the ratio of 35/65 (in molar %) in an aqueous solution.

(13) Cement dispersant comprising water-soluble vinyl copolymer with average numerical molecular weight of 15500 obtained by radical copolymerization of aforementioned polyetherester monomer (P-3), sodium methacrylate and sodium methallyl sulfonate at the ratio of 33/61/6 (in molar %) in an aqueous solution.

(14) Cement dispersant comprising water-soluble vinyl copolymer with average numerical molecular weight of 31000 obtained by radical copolymerization of aforementioned polyetherester monomer (P-4) and methacrylic acid at the ratio of 35/65 (in molar %) in an aqueous solution.

(15) Cement dispersant comprising water-soluble vinyl copolymer with average numerical molecular weight of 18000 obtained by radical copolymerization of aforementioned polyetherester monomer (P-4), sodium methacrylate and sodium methallyl sulfonate at the ratio of 33/61/6 (in molar %) in an aqueous solution.

(16) Cement dispersant comprising water-soluble vinyl copolymer with average numerical molecular weight of 37800 obtained by radical copolymerization of aforementioned polyetherester monomer (P-5) and methacrylic acid at the ratio of 35/65 (in molar %) in an aqueous solution.

(17) Cement dispersant comprising water-soluble vinyl copolymer with average numerical molecular weight of 23600 obtained by radical copolymerization of aforementioned polyetherester monomer (P-5), sodium methacrylate and sodium methallyl sulfonate at the ratio of 33/61/6 (in molar %) in an aqueous solution.

(18) Cement dispersant comprising water-soluble vinyl copolymer with average numerical molecular weight of 16200 obtained by radical copolymerization of aforementioned polyetherester monomer (P-6) and methacrylic acid at the ratio of 35/65 (in molar %) in an aqueous solution.

(19) Cement dispersant comprising water-soluble vinyl copolymer with average numerical molecular weight of 10400 obtained by radical copolymerization of aforementioned polyetherester monomer (P-6), sodium methacrylate and sodium methallyl sulfonate at the ratio of 33/61/6 (in molar %) in an aqueous solution.

(20) Cement dispersant comprising water-soluble vinyl copolymer with average numerical molecular weight of 24000 obtained by radical copolymerization of aforementioned polyetherester monomer (P-7) and methacrylic acid at the ratio of 35/65 (in molar %) in an aqueous solution.

(21) Cement dispersant comprising water-soluble vinyl copolymer with average numerical molecular weight of 15000 obtained by radical copolymerization of aforementioned polyetherester monomer (P-7), sodium methacrylate and sodium methallyl sulfonate at the ratio of 33/61/6 (in molar %) in an aqueous solution.

In what follows, the invention will be described by way of the results of test examples but it goes without saying that the invention is not limited to these examples. In the following, "parts" will mean "weight parts" and "%" will mean "weight %" unless specifically described to be otherwise.

Part 1: Production of Polyetherester Monomers

Test Example 1
(Production of Polyetherester Monomer (P-1))

Methoxy polyethyleneglycol (n=9) 1060 parts (2.5 moles), methacrylic acid 430 parts (5 moles), p-benzoquinone 2.2 parts and 98% concentrated sulfuric acid (same concentrated sulfuric acid hereinafter) 3.5 parts were placed inside a reactor. Temperature was increased gradually while stirring and pressure was lowered. While water being generated in the esterification reaction was removed out of the reacting system by distillation as azeotropic water/methacrylic acid mixture, the esterification reaction was continued for 2 hours under the condition of temperature at 125–130° C. and pressure at 12–2.5 kPa. Next, the remaining excess portion of methacrylic acid was removed by distillation by further reducing the pressure to obtain a product. This product was analyzed and identified as polyetherester monomer (P-1) with hydroxyl value 1.3, carboxyl value 1.2, esterification reaction rate (hereinafter calculated from the hydroxyl value) 99%.

Test Examples 2–7 and Comparison Example 1
(Production of Polyetherester Monomers (P-2)–(P-7) and (R-1))

As in Test Example 1, polyetherester monomers (P-2)–(P-7) as Test Examples 2–7 and polyetherester monomer (R-1) as Comparison Example 1 were produced.

Comparison Example 2
(Production of Polyetherester Monomer (r-1))

Methoxy polyethyleneglycol (n=9) 1060 parts (2.5 moles), methacrylic acid 430 parts (5 moles) and concentrated sulfuric acid 3.5 parts were placed inside a reactor to carry out esterification by raising the temperature while stirring but the reaction was discontinued because a large amount of insoluble gel came to be deposited during the process.

Comparison Example 3
(Production of Polyetherester Monomer (r-2))

Methoxy polyethyleneglycol (n=9) 1060 parts (2.5 moles), methacrylic acid 430 parts (5 moles), hydroquinone 2.2 parts and concentrated sulfuric acid 3.5 parts were placed inside a reactor to start an esterification reaction by raising the temperature while stirring but the reaction was discontinued because a large amount of insoluble gel came to be deposited about one hour after the start.

Comparison Example 4
(Production of Polyetherester Monomer (r-3))

Methoxy polyethyleneglycol (n=9) 1060 parts (2.5 moles), methacrylic acid 430 parts (5 moles), hydroquinone monomethyl ether 3.5 parts and concentrated sulfuric acid 3.5 parts were placed inside a reactor to start an esterification reaction by raising the temperature while stirring but the reaction was discontinued because a large amount of insoluble gel came to be deposited about 30 minutes after the start.

Comparison Example 5
(Production of Polyetherester Monomer (r-4))

Methoxy polyethyleneglycol (n=23) 1140 parts (1.1 moles), methacrylic acid 340 parts (3.9 moles), p-benzoquinone 0.3 parts and concentrated sulfuric acid 7.2 parts were placed inside a reactor to start an esterification reaction by raising the temperature while stirring but the reaction was discontinued because a large amount of insoluble gel came to be deposited about one hour the start.

Comparison Example 6
(Production of Polyetherester Monomer (r-5))

Methoxy polyethyleneglycol (n=23) 1140 parts (1.1 moles), methacrylic acid 340 parts (3.9 moles), phenothiazine 0.3 parts and concentrated sulfuric acid 7.2 parts were placed inside a reactor to start an esterification reaction by raising the temperature while stirring but the reaction was discontinued because a large amount of insoluble gel came to be deposited about one hour the start.

Comparison Example 7
(Production of Polyetherester Monomer (T-1))

Methoxy polyethyleneglycol (n=9) 1060 parts (2.5 moles), methacrylic acid 430 parts (5 moles), p-benzoquinone 2.2 parts, concentrated sulfuric acid 3.5 parts and benzene as solvent 1000 parts were placed inside a reactor to start an esterification reaction by raising the temperature while stirring while removing generated water by distillation. After the esterification reaction, the excess portion of methacrylic acid and the benzene used as solvent were removed by bubbling nitrogen to obtain a product. This product was analyzed and identified as polyetherester monomer (T-1) with hydroxyl value 1.3, carboxyl value 1.2, esterification reaction rate 99%.

Data on the production of these polyetherester monomers are summarized in Tables 1 and 2.

TABLE 1

| Examples | $R^3$ | A | $R^1$ | $R^2$ | PE/UA | Inhibitor | Acid Catalyst | Temp. (° C.) | Pressure (kPa) |
|---|---|---|---|---|---|---|---|---|---|
| Test Examples | | | | | | | | | |
| 1 P-1 | S-1 | A-1 | H | S-1 | 1/2.0 | I-1 (0.21) | C-1 (0.23) | 125–130 | 12–2.5 |
| 2 P-2 | S-1 | A-2 | H | S-1 | 1/3.5 | I-1 (0.18) | C-1 (0.49) | 125–130 | 10–2.5 |
| 3 P-3 | S-1 | A-3 | H | S-1 | 1/3.6 | I-1 (0.15) | C-1 (0.31) | 125–130 | 7–1.5 |
| 4 P-4 | S-2 | A-4 | H | S-1 | 1/3.2 | I-1 (0.13) | C-2 (0.68) | 125–130 | 5–1.5 |
| 5 P-5 | S-3 | A-5 | H | S-1 | 1/5.0 | I-1 (0.15) | C-3 (0.80) | 125–130 | 5–1.5 |
| 6 P-6 | S-1 | A-2 | H | S-1 | 1/3.5 | I-2 (0.19) | C-4 (0.47) | 125–130 | 10–2.5 |
| 7 P-7 | S-1 | A-3 | H | S-1 | 1/4.1 | I-3 (0.16) | C-5 (0.54) | 125–130 | 5–1.5 |
| Comp Examples | | | | | | | | | |
| 1 R-1 | S-1 | A-1 | H | S-1 | 1/2.0 | I-1 (1.0) | C-1 (0.23) | 125–130 | 12–2.5 |
| 2 r-1 | S-1 | A-1 | H | S-1 | 1/2.0 | — | C-1 (0.23) | *1 | *1 |

TABLE 1-continued

| Examples | R³ | A | R¹ | R² | PE/UA | Inhibitor | Acid Catalyst | Temp. (° C.) | Pressure (kPa) |
|---|---|---|---|---|---|---|---|---|---|
| 3 r-2 | S-1 | A-1 | H | S-1 | 1/2.0 | i-4 (0.21) | C-1 (0.23) | *1 | *1 |
| 4 r-3 | S-1 | A-1 | H | S-1 | 1/2.0 | i-5 (0.33) | C-1 (0.23) | *1 | *1 |
| 5 r-4 | S-1 | A-2 | H | S-1 | 1/3.5 | I-1 (0.02) | C-1 (0.49) | *1 | *1 |
| 6 r-5 | S-1 | A-2 | H | S-1 | 1/3.5 | I-2 (0.02) | C-1 (0.49) | *1 | *1 |
| 7 T-1 | S-1 | A-1 | H | S-1 | 1/2.0 | I-1 (0.21) | C-1 (0.23) | | |

In Table 1:

"Inhibitor" indicates "Polymerization inhibitor" and shows the kind and the weight % (in parentheses) used with respect to polyalkyleneglycol with a closed end.

"Acid Catalyst" shows the kind and the weight % (in parentheses) used with respect to the total amount of polyalkyleneglycol with a closed end and unsaturated carboxylic acid.

"PE/UA" indicates the molar ratio of polyalkyleneglycol with a closed end shown by Formula 1 and unsaturated carboxylic acid shown by Formula 2.

*1 indicates that the reaction was discontinued.

S-1: Methyl group

S-2: Benzyl group

S-3: Lauryl group

A-1: Residual group obtained by removing all hydroxyl groups from polyethyleneglycol with repetition number of oxyethylene groups equal to 9.

A-2: Residual group obtained by removing all hydroxyl groups from polyethyleneglycol with repetition number of oxyethylene groups equal to 23.

A-3: Residual group obtained by removing all hydroxyl groups from polyethyleneglycol with repetition number of oxyethylene groups equal to 75.

A-4: Residual group obtained by removing all hydroxyl groups from polyethyleneglycol with repetition number of oxyethylene groups equal to 90.

A-5: Residual group obtained by removing all hydroxyl groups from polyethyleneglycol with repetition number of oxyethylene groups equal to 120.

I-1: p-benzoquinone

I-2: phenothiazine

I-3: Mixture of p-benzoquinone/phenothiazine=50/50 as weight ratio i-4: Hydroquinone i-5: Hydroquinone monomethyl ether C-1: 98% concentrated sulfuric acid C-2: Mixed acid with 98% concentrated sulfuric acid and p-toluene sulfonic acid at weight ratio of 5/2.

C-3: Mixed acid with 98% concentrated sulfuric acid and p-toluene sulfonic acid at weight ratio of 5.5/2.5.

C-4: Mixed acid with 98% concentrated sulfuric acid and p-toluene sulfonic acid at weight ratio of 4.5/2.5.

C-5: Mixed acid with 98% concentrated sulfuric acid and p-toluene sulfonic acid at weight ratio of 4/3.

TABLE 2

| Examples | Abnormal Viscosity Increase | Generation of Gel | Esterification Reaction Ratio (%) |
|---|---|---|---|
| Test Examples | | | |
| 1 P-1 | A | A | 99 |
| 2 P-2 | A | A | 98 |
| 3 P-3 | A | A | 97 |
| 4 P-4 | A | A | 97 |
| 5 P-5 | A | A | 97 |
| 6 P-6 | A | A | 98 |
| 7 P-7 | A | A | 98 |
| Comparison Examples | | | |
| 1 R-1 | A | A | 98 |
| 2 r-1 | B | B | *2 |
| 3 r-2 | B | B | *2 |
| 4 r-3 | B | B | *2 |
| 5 r-4 | B | B | *2 |
| 6 r-5 | B | B | *2 |
| 7 T-1 | A | A | 99 |

In Table 2:

For the evaluation of presence/absence of abnormal viscosity increase:

A: No abnormal viscosity increase during esterification reaction

B: Presence of abnormal viscosity increase during esterification reaction

For the evaluation of presence/absence of gel generation:

A: No generation of insoluble gel during esterification reaction

B: Presence of generation of insoluble gel during esterification reaction *2: Esterification reaction ratio not measurable because esterification reaction was discontinued due to abnormal viscosity increase or generation of insoluble gel Part 2: Production of Water-soluble Vinyl Copolymers as Cement Dispersants Test Example 8
(Production of Water-soluble Vinyl Copolymer (D-1))

Polyetherester monomer (P-1), obtained in Part 1, 152 parts (0.306 moles), methacrylic acid 56 parts (0.65 moles), 3-mercaptopropionic acid 2.1 part and water 330 parts were added together and the atmosphere was replaced with nitrogen after they were dissolved uniformly by stirring. While the temperature of the reacting system was maintained at 80° C. in the nitrogen environment by means of a warm bath, polymerization was started by dropping 20% aqueous solution of sodium persulfate 8 parts. The polymerization reaction was continued for 5 hours and an aqueous solution of water-soluble vinyl copolymer was obtained. This water-soluble vinyl copolymer was analyzed and identified as water-soluble vinyl copolymer (D-1) with average numerical molecular weight of 12500 having 35 molar % of component unit derived from polyetherester monomer (P-1) and 65 molar % of component unit derived from methacrylic acid.

Test Example 9
(Production of Water-soluble Vinyl Copolymer (D-2))

Polyetherester monomer (P-1), obtained in Part 1, 150 parts (0.30 moles), methacrylic acid 55 parts (0.64 moles), sodium methallylsulfonate 13 parts (0.082 moles), water 330 parts and aqueous solution of sodium hydroxide 80 parts were added together and the atmosphere was replaced with nitrogen after they were dissolved uniformly by stirring. While the temperature of the reacting system was maintained at 60° C. in the nitrogen environment by means of a warm bath, polymerization was started by dropping 20% aqueous solution of sodium persulfate 10 parts. The polymerization reaction was continued for 6 hours and 30% aqueous solution of sodium hydroxide was added thereafter for a complete neutralization to obtain an aqueous solution of water-soluble vinyl copolymer. This water-soluble vinyl copolymer was analyzed and identified as water-soluble vinyl copolymer (D-2) with average numerical molecular weight of 8800 having 33 molar % of component unit derived from polyetherester monomer (P-1), 61 molar % of component unit derived from methacrylic acid and 6 molar % of component unit derived from sodium methallylsulfonate.

Test Examples 10–21
(Production of Water-soluble Vinyl Copolymers (D-3)–(D-14))

Water-soluble vinyl copolymers (D-3)–(D-14) were produced as in Test Example 8 or 9. The details are shown in Table 3.

TABLE 3

| Test Examples | Water-Soluble Vinyl Copolymer | Ratio of Copolymerization (molar %) | | | | Average Numerical Molecular Weight |
|---|---|---|---|---|---|---|
| | | a | b | c | d | |
| 8 | D-1 | P-1/35 | 65 | — | — | 12500 |
| 9 | D-2 | P-1/33 | — | 61 | 6 | 8800 |
| 10 | D-3 | P-2/35 | 65 | — | — | 17000 |
| 11 | D-4 | P-2/33 | — | 61 | 6 | 9600 |
| 12 | D-5 | P-3/35 | 65 | — | — | 25300 |
| 13 | D-6 | P-3/33 | — | 61 | 6 | 15500 |
| 14 | D-7 | P-4/35 | 65 | — | — | 31000 |
| 15 | D-8 | P-4/33 | — | 61 | 6 | 18000 |
| 16 | D-9 | P-5/35 | 65 | — | — | 37800 |
| 17 | D-10 | P-5/33 | — | 61 | 6 | 23600 |
| 18 | D-11 | P-6/35 | 65 | — | — | 16200 |
| 19 | D-12 | P-6/33 | — | 61 | 6 | 10400 |
| 20 | D-13 | P-7/35 | 65 | — | — | 24000 |
| 21 | D-14 | P-7/33 | — | 61 | 6 | 15000 |

In Table 3:
a: Polyetherester monomer/molar %
b: Methacrylic acid
c: Sodium methacrylate
d: Sodium methallyl sulfonate Comparison Example 8
(Production of Water-soluble Vinyl Copolymer (DR-1))

Water-soluble vinyl copolymer (DR-1) was produced as Comparison Example 8 in the same way as described in Test Example 8 for the production of water-soluble vinyl copolymer (D-1) except that "polyetherester monomer (P-1) 152 parts" was replaced by "polyetherester monomer (R-1), obtained in Part 1, 152 parts".

Comparison Example 9
(Production of Water-soluble Vinyl Copolymer (DT-1))

Water-soluble vinyl copolymer (DT-1) was produced as Comparison Example 9 in the same way as described in Test Example 8 for the production of water-soluble vinyl copolymer (D-1) except that "polyetherester monomer (P-1) 152 parts" was replaced by "polyetherester monomer (T-1), obtained in Part 1, 152 parts".

Comparison Example 10
(Production of Water-soluble Vinyl Copolymer (DT-2))

Water-soluble vinyl copolymer (DT-2) was produced as Comparison Example 8 in the same way as described in Test Example 9 for the production of water-soluble vinyl copolymer (D-2) except that "polyetherester monomer (P-1) 150 parts" was replaced by "polyetherester monomer (T-1), obtained in Part 1, 150 parts".

Part 3: Preparation and Evaluation of Concrete
Preparation of Concrete Samples

Concrete samples were prepared as follows under the conditions shown in Table 4.

Normal portland cement (specific weight=3.16; braine value=3300), fine aggregates (Ooi-gawa River sand with specific weight=2.63) and coarse aggregates (crushed stones from Okazaki with specific weight=2.63) were sequentially added into a pan-type forced kneading mixer with capacity 50 liters and subjected to a free kneading process for 15 seconds. Next, the water-soluble vinyl copolymers produced in Part 2 as cement dispersants were each added with water and kneaded at a rate of 0.1–1.5 weight % with respect to the cement (as converted to solid component) such that the target slump would be within the range of 21±1 cm, and the mixture was kneaded for 2 minutes. An agent for controlling the amount of air was also added in each case such that the target amount of air would be 4.0–5.0%.

TABLE 4

| Water/cement ratio (%) | Ratio of fine aggregates (%) | Unit amount (kg/m$^3$) | | |
|---|---|---|---|---|
| | | Water | Cement | Fine aggregates | Coarse aggregates |
| 50 | 49 | 165 | 330 | 867 | 960 |

Evaluation of Concrete Samples

Slump of each concrete sample prepared was evaluated as follows, both immediately after the kneading (t=0) and after it was left quietly for 60 minutes (t=60) according to JIS-A1101 (Japanese Industrial Standard). The results of evaluation are shown in Table 5.

Slump loss: ((Slump at t=60)/(Slump at t=0))×100
Amount of air: Measured according to JIS-A1128
Compressive Strength (CS): Measured according to JIS-A1108.

TABLE 5

| | Cement Dispersant | | t = 0 | | t = 60 | | Slump | CS (N/mm$^2$) | |
|---|---|---|---|---|---|---|---|---|---|
| No. | Type | Amount (part) | Slump (cm) | Air (%) | Slump (cm) | Air (%) | Loss (%) | 7 days | 28 days |
| 1 | D-1 | 0.22 | 21.7 | 4.5 | 18.0 | 4.3 | 82.9 | 34.0 | 45.2 |
| 2 | D-2 | 0.24 | 21.3 | 4.5 | 20.0 | 4.4 | 93.9 | 34.2 | 45.5 |

TABLE 5-continued

| | Cement Dispersant | | t = 0 | | t = 60 | | Slump | | |
|---|---|---|---|---|---|---|---|---|---|
| | | Amount | Slump | Air | Slump | Air | Loss | CS (N/mm²) | |
| No. | Type | (part) | (cm) | (%) | (cm) | (%) | (%) | 7 days | 28 days |
| 3 | D-3 | 0.21 | 21.5 | 4.3 | 18.3 | 4.3 | 85.1 | 34.1 | 45.0 |
| 4 | D-4 | 0.22 | 21.8 | 4.2 | 19.9 | 4.2 | 91.3 | 34.5 | 45.3 |
| 5 | D-5 | 0.20 | 21.3 | 4.4 | 18.1 | 4.0 | 85.0 | 35.0 | 46.3 |
| 6 | D-6 | 0.21 | 21.1 | 4.5 | 18.8 | 4.4 | 89.1 | 34.7 | 45.2 |
| 7 | D-7 | 0.23 | 21.6 | 4.6 | 18.5 | 4.5 | 85.6 | 34.4 | 45.5 |
| 8 | D-8 | 0.24 | 21.8 | 4.5 | 19.7 | 4.2 | 90.4 | 34.2 | 45.3 |
| 9 | D-9 | 0.26 | 21.4 | 4.4 | 19.5 | 4.3 | 91.1 | 34.6 | 45.6 |
| 10 | D-10 | 0.28 | 21.2 | 4.7 | 20.0 | 4.6 | 94.3 | 34.0 | 45.1 |
| 11 | D-11 | 0.22 | 21.7 | 4.6 | 18.9 | 4.2 | 87.1 | 34.8 | 46.0 |
| 12 | D-12 | 0.23 | 21.3 | 4.5 | 20.1 | 4.1 | 94.3 | 35.0 | 46.2 |
| 13 | D-13 | 0.21 | 21.5 | 4.3 | 18.2 | 4.2 | 84.7 | 34.6 | 45.7 |
| 14 | D-14 | 0.23 | 21.6 | 4.6 | 19.5 | 4.4 | 90.3 | 34.3 | 45.1 |
| 15 | DR-1 | 0.43 | 21.2 | 4.5 | 13.7 | 4.2 | 64.6 | 31.2 | 40.9 |
| 16 | DT-1 | 0.22 | 21.5 | 4.5 | 17.8 | 4.1 | 82.8 | 34.0 | 45.0 |
| 17 | DT-2 | 0.24 | 21.2 | 4.5 | 19.8 | 4.4 | 93.4 | 34.1 | 45.5 |

In Table 5:

"7 days" and "28 days": Age of tested product

Amount of added cement dispersant is shown as that of water-soluble vinyl copolymer in solid form with respect to 100 parts of cement.

As can be understood from the above, the present invention makes it possible to produce polyetherester monomers of a high quality in the absence of any solvent and to provide cement dispersants with improved properties comprising water-soluble vinyl copolymers which can be produced from such polyetherester monomers are an intermediate product.

What is claimed is:

1. A method of producing polyetherester monomer shown by Formula 3, said method comprising the step of causing an esterification reaction of polyalkyleneglycol with a closed end shown by Formula 1 and unsaturated carboxylic acid shown by Formula 2 by using an acid catalyst under a heated and reduced-pressure condition in the absence of solvents and in the presence of one selected from the group consisting of p-benzoquinone, phenothiazine and a mixture thereof in an amount of 0.03–0.5 weight % of said polyalkyleneglycol with a closed end while distilling away generated water, wherein said Formula 1, said Formula 2 and said Formula 3 are respectively:

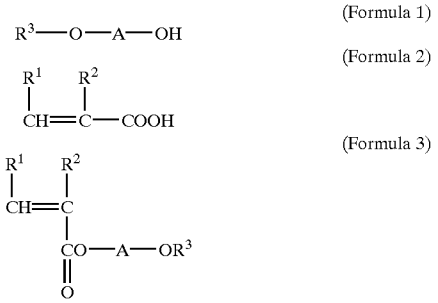

where $R^1$ and $R^2$ are each H or methyl group, $R^3$ is one selected from the group consisting of alkyl groups with 1–22 carbon atoms, benzyl group, phenyl group and alkylphenyl groups each having alkyl group with 1–12 carbon atoms, and A is residual group produced by removing all hydroxyl groups from polyalkyleneglycol with repetition number of oxyalkylene units 5–250, said oxyalkylene units consisting either only of oxyethylene units or of both oxyethylene units and oxypropylene units.

2. The method of claim 1 wherein said polyalkyleneglycol with a closed end and said unsaturated carboxylic acid are used at a molar ratio of 1/1.5–1/7 and an excess amount of said unsaturated carboxylic acid is removed by distillation after said esterification reaction.

3. The method of claim 2 wherein p-benzoquinone is caused to be present in an amount which is 0.1–0.25 weight % of said polyalkyleneglycol with a closed end.

4. The method of claim 2 wherein said esterification reaction is carried out while the temperature of said polyalkyleneglycol with a closed end and said unsaturated carboxylic acid is increased gradually or in a stepwise manner within 105–135° C. and the pressure thereof is reduced gradually or in a stepwise manner within 15–0.5 kPa.

5. The method of claim 3 wherein said esterification reaction is carried out while the temperature of said polyalkyleneglycol with a closed end and said unsaturated carboxylic acid is increased gradually or in a stepwise manner within 105–135° C. and the pressure thereof is reduced gradually or in a stepwise manner within 15–0.5 kPa.

6. The method of claim 4 wherein said acid catalyst is added in an amount which is 0.2–1.5 weight % of the total amount of said polyalkyleneglycol with a closed end and said unsaturated carboxylic acid.

7. The method of claim 5 wherein said acid catalyst is added in an amount which is 0.2–1.5 weight % of the total amount of said polyalkyleneglycol with a closed end and said unsaturated carboxylic acid.

8. The method of claim 6 wherein A in said Formula 1 for said polyalkyleneglycol with a closed end is residual group produced by removing all hydroxyl groups from polyalkyleneglycol with repetition number of oxyalkylene units 5–250, said oxyalkylene units consisting only of oxyethylene units.

9. The method of claim 7 wherein A in said Formula 1 for said polyalkyleneglycol with a closed end is residual group produced by removing all hydroxyl groups from polyalkyleneglycol with repetition number of oxyalkylene units 5–250, said oxyalkylene units consisting only of oxyethylene units.

10. A cement dispersant comprising water-soluble vinyl copolymer produced by a first step and a second step, said first step consisting of producing polyetherester monomer shown by Formula 3 by causing an esterification reaction of polyalkyleneglycol with a closed end shown by Formula 1 and unsaturated carboxylic acid shown by Formula 2 by using an acid catalyst under a heated and reduced-pressure condition in the absence of solvents and in the presence of one selected from the group consisting of p-benzoquinone, phenothiazine and a mixture thereof in an amount of 0.03–0.5 weight % of said polyalkyleneglycol with a closed end while distilling away generated water, wherein said Formula 1, said Formula 2 and said Formula 3 are respectively:

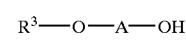  (Formula 1)

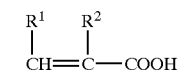  (Formula 2)

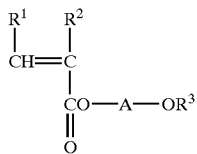  (Formula 3)

where $R^1$ and $R^2$ are each H or methyl group, $R^3$ is one selected from the group consisting of alkyl groups with 1–22 carbon atoms, benzyl group, phenyl group and alkylphenyl groups each having alkyl group with 1–12 carbon atoms, and A is residual group produced by removing all hydroxyl groups from polyalkyleneglycol with repetition number of oxyalkylene units 5–250, said oxyalkylene units consisting either only of oxyethylene units or of both oxyethylene units and oxypropylene units; and said second step consisting of
producing said water-soluble vinyl copolymer by radical copolymerization of said polyetherester monomer produced in said first step and vinyl monomer inside an aqueous solution, said vinyl monomer being copolymerizable with said polyetherester monomer.

11. The cement dispersant of claim 10 wherein said polyalkyleneglycol with a closed end and said unsaturated carboxylic acid are used at a molar ratio of 1/1.5–1/7 and an excess amount of said unsaturated carboxylic acid is removed by distillation after said esterification reaction in said first step.

12. The cement dispersant of claim 11 wherein p-benzoquinone is caused to be present in an amount which is 0.1–0.25 weight % of said polyalkyleneglycol with a closed end in said first step.

13. The cement dispersant of claim 11 wherein said esterification reaction in said first step is carried out while the temperature of said polyalkyleneglycol with a closed end and said unsaturated carboxylic acid is increased gradually or in a stepwise manner within 105–135° C. and the pressure thereof is reduced gradually or in a stepwise manner within 15–0.5 kPa.

14. The cement dispersant of claim 12 wherein said esterification reaction in said first step is carried out while the temperature of said polyalkyleneglycol with a closed end and said unsaturated carboxylic acid is increased gradually or in a stepwise manner within 105–135° C. and the pressure thereof is reduced gradually or in a stepwise manner within 15–0.5 kPa.

15. The cement dispersant of claim 13 wherein said acid catalyst is added in said first step in an amount which is 0.2–1.5 weight % of the total amount of said polyalkyleneglycol with a closed end and said unsaturated carboxylic acid.

16. The cement dispersant of claim 14 wherein said acid catalyst is added in said first step in an amount which is 0.2–1.5 weight % of the total amount of said polyalkyleneglycol with a closed end and said unsaturated carboxylic acid.

17. The cement dispersant of claim 15 wherein A in said Formula 1 for said polyalkyleneglycol with a closed end used in said first step is residual group produced by removing all hydroxyl groups from polyalkyleneglycol with repetition number of oxyalkylene units 5–250, said oxyalkylene units consisting only of oxyethylene units.

18. The cement dispersant of claim 16 wherein A in said Formula 1 for said polyalkyleneglycol with a closed end used in said first step is residual group produced by removing all hydroxyl groups from polyalkyleneglycol with repetition number of oxyalkylene units 5–250, said oxyalkylene units consisting only of oxyethylene units.

19. The cement dispersant of claim 17 wherein (meth) acrylic acid and/or salt thereof is used as said vinyl monomer in said second step.

20. The cement dispersant of claim 18 wherein (meth) acrylic acid and/or salt thereof is used as said vinyl monomer in said second step.

21. The cement dispersant of claim 17 wherein (meth) acrylic acid and/or salt thereof and methallyl sulfonate are used as said vinyl monomer in said second step.

22. The cement dispersant of claim 18 wherein (meth) acrylic acid and/or salt thereof and methallyl sulfonate are used as said vinyl monomer in said second step.

* * * * *